United States Patent [19]

Heymes et al.

[11] 4,374,834
[45] Feb. 22, 1983

[54] NOVEL COMPOUNDS

[75] Inventors: Rene Heymes, Romainville; Andre Lutz, Strasbourg, both of France

[73] Assignee: Roussel Uclaf, Paris, France

[21] Appl. No.: 247,743

[22] Filed: Mar. 26, 1981

Related U.S. Application Data

[62] Division of Ser. No. 26,767, Apr. 3, 1979, Pat. No. 4,287,193.

[30] Foreign Application Priority Data

Apr. 7, 1978 [FR] France ............... 78 10287

[51] Int. Cl.³ .................................. A61K 31/545
[52] U.S. Cl. .............................. 424/246; 544/28
[58] Field of Search ............... 544/28; 424/246

[56] References Cited

U.S. PATENT DOCUMENTS 4,278,793 7/1981 Durckheimer et al. ............ 544/28

Primary Examiner—Paul M. Coughlan, Jr.
Attorney, Agent, or Firm—Hammond & Littell, Weissenberger and Muserlian

[57] ABSTRACT

Novel syn isomers of 7-[2-(2-amino-4-thiazolyl)-2-(carboxymethyloxyimino)-acetamido]-ceph-3-eme-4-carboxylic acid compounds of the formula

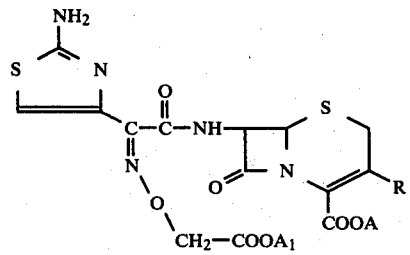

wherein R is selected from the group consisting of alkyl of 1 to 3 carbon atoms and $-CH_2-S-R_1$, $R_1$ is an optionally substituted heterocyclic of 5 to 6 chain components with 1 to 4 heteroatoms selected from the group consisting of oxygen, sulfur and nitrogen, A is selected from the group consisting of hydrogen, alkali metal, alkaline earth metal, magnesium, $-NH_4$, an easily cleavable ester and a non-toxic, pharmaceutically acceptable organic amine, $A_1$ is selected from the group consisting of alkyl of 1 to 3 carbon atoms, hydrogen, alkali metal, alkaline earth metal, magnesium, $-NH_4$, an easily cleavable ester and a non-toxic, pharmaceutically acceptable organic amine and non-toxic, pharmaceutically acceptable acid addition salts thereof having antibiotic activity and their preparation and intermediates therefor.

9 Claims, No Drawings

NOVEL COMPOUNDS

PRIOR APPLICATION

This application is a divisional application of our copending, commonly assigned U.S. patent application Ser. No. 26,767, filed Apr. 3, 1979, now U.S. Pat. No. 4,287,193.

STATE OF THE ART

Related cephalosporanic acid compounds are described in French Patents No. 2,137,899; No. 2,294,690; No. 2,348,218; No. 2,348,219; No. 2,255,076 and 2,355,849 and commonly assigned U.S. patents applications Ser. No. 761,270 filed Jan. 21, 1977, now abandoned in favor of continuation-in-part application Ser. No. 817,114 filed July 19, 1977 and now U.S. Pat. No. 4,152,432 and Ser. No. 796,315 filed May 12, 1977 and Ser. No. 886,421 filed Mar. 14, 1978.

OBJECTS OF THE INVENTION

It is an object of the invention to provide the novel cephalosporanic acid derivatives of formula I and their non-toxic, pharmaceutically acceptable acid addition salts and a novel process and novel intermediates for their preparation.

It is another object of the invention to provide novel antibacterial compositions and a novel method of treating bacterial infections in warm-blooded animals.

These and other objects and advantages of the invention will become obvious from the following detailed description.

THE INVENTION

The novel products of the invention are selected from the group consisting of the syn isomers of 7-[2-(2-amino-4-thiazolyl)-2-carboxymethyloxyimino)-acetamido]-ceph-3-eme-4-carboxylic acid compounds of the formula

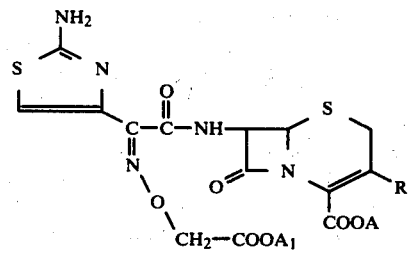

wherein R is selected from the group consisting of alkyl of 1 to 3 carbon atoms and $-CH_2-S-R_1$, $R_1$ is an optionally substituted heterocyclic of 5 to 6 chain components with 1 to 4 heteroatoms selected from the group consisting of oxygen, sulfur and nitrogen, A is selected from the group consisting of hydrogen, alkali metal, alkaline earth metal, magnesium, $-NH_4$, an easily cleavable ester and a non-toxic, pharmaceutically acceptable organic amine, $A_1$ is selected from the group consisting of alkyl of 1 to 3 carbon atoms, hydrogen, alkali metal, alkaline earth metal, magnesium, $-NH_4$, an easily cleavable ester and a non-toxic, pharmaceutically acceptable organic amine and non-toxic, pharmaceutically acceptable acid addition salts thereof.

Examples of suitable R groups are methyl, ethyl, propyl, and isopropyl. Examples of suitable heterocyclics of $R_1$ are 1,2,3-thiadiazolyl, 1,2,5-thiadiazolyl, 1,2,4-thiadiazolyl, 1,3,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, all optionally substituted with at least one member of the group consisting of methyl, ethyl, propyl, isopropyl, methoxy, ethoxy, propoxy, isopropoxy, amino, hydroxycarbonylmethyl, dimethylaminoethyl and diethylaminoethyl.

Examples of specific heterocyclics of $R_1$ are [selected from the group consisting of 1-methyltetrazolyl, 2-methyl-1,3,4-thiadiazolyl, 3-methyl-1,2,4-thiadiazolyl, 3-methoxy-1,2,4-thiadiazolyl, 1,3,4-thiadiazol-5-yl, 2-amino-1,3,4-thiadiazolyl, 3-hydroxy-carbonylmethyl-1,2,4-thiadiazolyl, 5-methoxy-1,2,4-thiadiazolyl, 4-methyl-5-hydroxycarbonylmethyl-1,3,-thiazolyl and 1-dimethylaminoethyltetrazol-5-yl].

Examples of suitable A and $A_1$ salt groups are alkali metals such as sodium, potassium and lithium, alkaline earth metals such as calcium, magnesium, $-NH_4$ and non-toxic, pharmaceutically acceptable organic amines such as triethylamine, diethylamine, trimethylamine, methylamine, propylamine, N,N-dimethylethanolamine, tris(hydroxymethyl)-aminomethane, ethanolamine, pyridine, picoline, dicyclohexylamine, N,N'-dibenzylethylenediamine, morpholine, benzylamine, procaine, lysine, arginine, histidine and N-methyl glucamine. A may also be methyl, ethyl, propyl and isopropyl.

Examples of easily cleavable ester groups for A and $A_1$ are [selected from the group consisting of methoxymethyl, ethoxymethyl, isopropoxymethyl, α-methoxyethyl, α-ethoxyethyl, methylthiomethyl, ethylthiomethyl, isopropylthiomethyl, pivaloyloxymethyl, acetoxymethyl, propionyloxymethyl, isobutyryloxymethyl, isovaleryloxymethyl, propionyloxyethyl, isovaleryloxyethyl, 1-acetoxyethyl, 1-acetoxypropyl, 1-acetoxybutyl, 1-acetoxyhexyl and 1-acetoxyheptyl].

Examples of suitable acids for the non-toxic, pharmaceutically acceptable acid addition salts are mineral acids such as hydrochloric acid, hydrobromic acid, sulfuric acid and phosphoric acid and organic acids such as acetic acid, trifluoroacetic acid, maleic acid, tartaric acid, methane sulfonic acid, benzenesulfonic acid and p-toluenesulfonic acid.

Among the preferred compounds of formula I are those wherein R is selected from the group consisting of methyl, 1-methyl-tetrazol-5-yl thiomethyl and 5-methyl-1,3,4-thiadiazol-2-ylthiomethyl.

Specific preferred compounds of formula I are selected from the group consisting of the syn isomer of 3-methyl-7-[2-(2-amino-4-thiazolyl)-2-(carboxymethyloxyimino)-acetamido]ceph-3-eme-4-carboxylic acid, the syn isomer of 3-[(1-methyl-tetrazol-5-yl)-thiomethyl]-7-[2-(2-amino-4-thiazolyl)-2-(carboxymethyloxyimino)-acetamido]-ceph-3-eme-4-carboxylic acid and the syn isomer of 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylic acid and their alkali metal, alkaline earth metal, magnesium, $-NH_4$ and organic amine salts and easily cleavable esters.

The novel products of formula I may exist in the indicated form or in the form of the formula

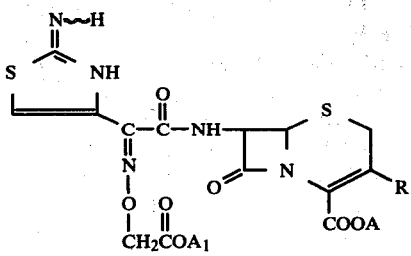

$I_z$

The novel process of the invention for the preparation of the compounds of formula I comprises reacting a compound of the formula

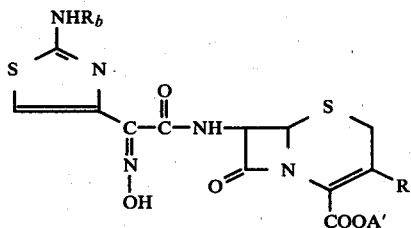

II wherein R has the above definition, $R_b$ is a amino protective group and A' is selected from the group consisting of hydrogen and an easily removable ester group with a compound of the formula

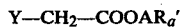

$$Y—CH_2—COOR_a'$$  III wherein Y is selected from the group consisting of halogen, sulfonate and sulfate groups and $R_a'$ is selected from the group consisting of alkyl of 1 to 3 carbon atoms and an easily removable ester to obtain a compound of the formula

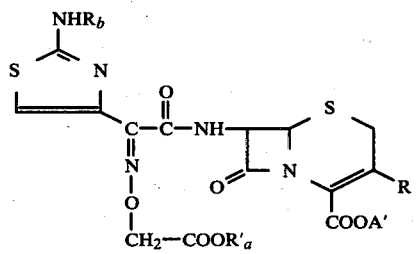

IV and treating the latter with at least one agent of the group consisting of hydrolysis agent, thiourea and hydrogenolysis agent to obtain a compound of the formula

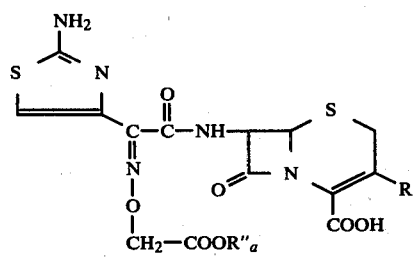

$I_a$ wherein $R_a''$ is selected from the group consisting of hydrogen and alkyl of 1 to 3 carbon atoms, which is a compound of formula I wherein A is hydrogen and $A_1$ is $R_a''$, which may be esterified or salified by conventional means.

The amino protective group $R_b$ may be alkyl of 1 to 6 carbon atoms, especially tert.-butyl or tert.-amyl; $R_b$ may also be acyl of aliphatic, aromatic or heterocyclic carboxylic acids or a carbamoyl; alkanoyl groups of 1 to 7 carbon atoms such as formyl, acetyl, propionyl, butyryl, isobutyryl, valeryl, isovaleryl, oxalyl, succinyl and pivaloyl can be especially mentioned. These alkanoyl groups are optionally substituted with a halogen such as bromine, iodine, chlorine or fluorine and groups such as chloroacetyl, dichloroacetyl, trichloroacetyl, trifluoroacetyl or bromoacetyl can be mentioned.

$R_b$ may also be lower alkoxycarbonyl such as methoxycarbonyl, ethoxycarbonyl, propoxycarbonyl, butoxycarbonyl, tert.-butoxycarbonyl, 1-cyclopropylethoxycarbonyl, isopropoxycarbonyl, pentyloxycarbonyl, tert.-pentyloxycarbonyl, hexyloxycarbonyl, benzoyl, toluolyl, naphthoyl, phthaloyl, mesyl, phenylacetyl and phenylpropionyl and aralkoxycarbonyl such as benzyloxycarbonyl. Also useful for $R_b$ are lower aralkyl groups such as benzyl, 4-methoxybenzyl, phenethyl, trityl, 3,4-dimethoxy-benzyl and benzhydryl and haloalkyl groups such as trichloroethyl. Also useful are chlorobenzoyl, p-nitrobenzyl, p-tert.-butyl-benzoyl, phenoxyacetyl, caprylyl, n-decanoyl, acryloyl, methylcarbamoyl, phenylcarbamoyl, naphthylcarbamoyl as well as their corresponding thiocarbamoyls. The list is not intended to be exhaustive since other amine protecting groups may be used, especially those known in peptide chemistry.

The esters groups of A' and $R_a'$ that are easily removable may be formed with butyl, isobutyl, tert.-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl or 2-butyryloxyethyl, for example. Equally useful are 2-iodoethyl, $\beta,\beta,\beta$-trichloroethyl, vinyl, allyl, ethynyl, propynyl, benzyl, 4-methoxybenzyl, 4-nitrobenzyl, phenethyl, trityl, benzhydryl, 3,4-dimethoxyphenyl, phenyl, 4-chlorophenyl, tolyl and tert.-butylphenyl.

Examples of Y are halogens such as chlorine, bromine or iodine or a sulfonate or a sulfate group such as mesylate or tosylate.

The reaction of the compounds of formulae II and III is preferably effected in the presence of a base such as triethylamine, potassium carbonate, sodium hydroxide, potassium hydroxide, sodium hydride and other bases.

The removal of the $R_b$ group is effected by hydrolysis either under basic or acidic conditions or with hydrazine. Acid hydrolysis is preferably used to remove alkoxycarbonyl and cycloalkoxycarbonyl groups optionally substituted such as tert.-pentyloxycarbonyl or tert.-butoxycarbonyl as well as optionally substituted aralkoxycarbonyl groups such as benzyloxycarbonyl, trityl, tert.-butyl or 4-methoxybenzyl. The acid is preferably selected from group consisting of hydrochloric acid, benzene sulfonic acid, p-toluene sulfonic acid, formic acid, trifluoroacetic acid as well as other mineral and organic acids.

The basic hydrolysis is preferably used to eliminate acyl groups such as trifluoroacetyl. The base is preferably a mineral base such as alkali metal hydroxides like sodium hydroxide or potassium hydroxide, magnesia, baryta, alkali metal carbonates or bicarbonates like sodium carbonate, sodium bicarbonate, potassium carbonate or potassium bicarbonate. Equally useful are sodium acetate and potassium acetate as well as other bases.

The hydrolysis with hydrazine is preferably used to remove phthaloyl groups. The zinc-acetic acid system may also be used to remove the $R_b$ group, especially for trichloro ethyl. Hydrogen in the presence of a catalyst is preferably used to remove benzhydryl and benzyloxycarbonyl. Chloroacetyl is preferably removed by thiourea in acid or neutral medium using the procedure of Masaki [J.A.C.S., Vol. 90 (1958), p. 4508]. Other known methods may be used to remove the protective amine group.

Among the preferred groups are formyl, acetyl, ethoxycarbonyl, mesyl, trifluoroacetyl, trityl and chloroacetyl. The preferred acid is formic acid or trifluoroacetic acid.

The removal of A′ and $R_a'$ when one at least of the groups is an easily removed ester is conducted under the same conditions as those described for the removal of $R_b$. Basic or acidic hydrolysis can be especially mentioned. Acid hydrolysis is preferably used to remove optionnally substituted alkyl or aralkyl and is preferably conducted with hydrochloric acid, formic acid, trifluoroacetic acid or p-toluene sulfonic acid. The other groups of A′ and $R_a'$ are removed by processes known to those skilled in the art. The conditions are preferably moderate such as at room temperature or with slight heating. Obviously, when $R_b$, A′ and $R_a'$, for example, are different types of removable groups, the compounds of formula IV may be treated with more than one of the above agents.

The compounds of formula $I_a$ may be salified by known methods such as by reacting the acid or a solvate thereof (i.e. with ethanol) with a mineral base such as sodium hydroxide, potassium hydroxide, sodium bicarbonate and potassium bicarbonate. Salts of mineral acids such as trisodium phosphate can also be used. Equally useful are salts of organic acids such as sodium salts of saturated or unsaturated aliphatic carboxylic acids of 1 to 18, preferably 2 to 10, carbon atoms. The aliphatic groups may be interrupted with one or more heteroatoms such as oxygen or sulfur and may be substituted with aryl such as phenyl, thienyl or furyl or at least one hydroxy, or at least one halogen such as fluorine, chlorine, or bromine, especially chlorine or at least one carbonyl or lower alkoxycarbonyl, group, preferably methoxycarbonyl, ethoxycarbonyl or propyloxycarbonyl or at least one aryloxy, preferably phenoxy. Also useful are salts of sufficiently soluble aromatic acids such as substituted benzoic acids, especially with lower alkyl substituents. Lower alkyl is intended to include 1 to 6 carbon atoms.

Examples of suitable organic acids are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, monoethyl ether of adipic acid, hexanoic acid, heptanoic acid, decanoic acid, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethyl benzoic acid and 1-propyl-benzoic acid. The preferred sodium salts are sodium acetate, sodium 2-ethylhexanoate and sodium diethylacetate.

The salification may also be effected with an organic base such as triethylamine, diethylamine, trimethylamine, propylamine, N,N-dimethyl-ethanolamine, tris-(hydroxymethyl)-aminomethane, arginine, lysine, methylamine, ethanolamine, pyridine, picoline, dicyclohexylamine, procaine, histidine, N-methyl-glucamine, morpholine and benzylamine. The salification is preferably effected in at least one solvent such as water, ether, methanol, ethanol or acetone.

The salification may result in salts in amorphous or crystalline form depending upon the conditions used. Crystalline salts are preferably formed by reacting the free acids with salts of the above aliphatic carboxylic acids, especially sodium acetate.

The eventual esterification of the compounds of formula $I_a$ may be effected by classical known conditions, generally reacting an acid of formula $I_a$ with a compound of the formula Rd-Z wherein Rd is an ester group and Z is —OH or a halogen such as chlorine, bromine or iodine.

The compounds of formula I may also be prepared by reacting a compound of the formula

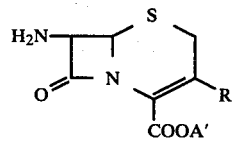

V wherein R has the above definition and A′ is selected from the group consisting of hydrogen and an easily removable ester with a syn isomer of a compound of the formula

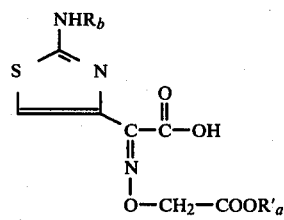

VI or a functional acid derivative thereof wherein $R_b$ is an amine protective group and $R_a'$ is selected from the group consisting of alkyl of 1 to 3 carbon atoms and an easily removable ester group to obtain a compound of the formula

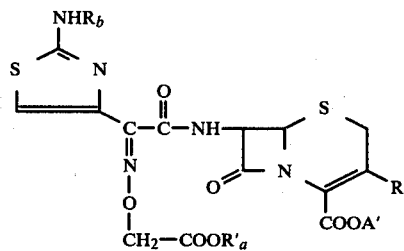

IV and treating the latter with at least one member of the group consisting of hydrolysis agent, thiourea and hydrogenolysis agent to obtain a compound of formula $I_a$ which is a compound of formula I wherein A is hydrogen and $A_1$ is alkyl of 1 to 3 carbon atoms or hydrogen and the resulting compound may be esterified or salified by known methods.

In a preferred mode of the said process, the product of formula V is reacted with a functional derivative of a compound of formula VI such as the acid halide, symetrical or mixed acid anhydride, amide or active ester. An example of a mixed anhydride is formed with isobutyl chloroformate and an active ester example is 2,4-dinitrophenol. The acid halide is preferably acid chloride or acid bromide. Other derivatives are the acid azide or amide. The acid anhydride may be formed in situ by reaction with N,N'-disubstituted carbodiimides such as N,N'-dicyclohexylcarbodiimide.

The acylation is preferably effected in an organic solvent such as methylene chloride but other solvents such as tetrahydrofuran, chloroform or dimethylformamide may be used. When the acid halide or the mixed anhydride with isobutyl chloroformate are used, the reaction is preferably effected in the presence of a base such as sodium hydroxide, potassium hydroxide, sodium carbonate, sodium bicarbonate, potassium carbonate, potassium bicarbonate, sodium acetate, triethylamine, pyridine, morpholine or N-methylmorpholine. The reaction is preferably effected at or below room temperature.

The transformation of the products of formula IV into compounds of formula $I_a$ and the salification or esterification of the compounds of formula $I_a$ may be effected by the conditions described above. $R_b$ protective groups are preferred as indicated before.

The antibiotic compositions of the invention are comprised of an antibiotically effective amount of at least one compound of formula I and thier non-toxic, pharmaceutically acceptable acid addition salts and an inert pharmaceutical carrier. The compositions may be in the form of tablets, dragees, gelules, granules, suppositories, injectable solutions or suspensions, creams, pomades, gels, etc. prepared in the usual fashion, and especially in the form of a powder intended to be dissolved extemporaneously in an appropriate vehicle, for example apyrogenetic sterile water.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers. The compositions of the invention possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefor useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

Among the preferred compositions of the invention are those wherein R is selected from the group consisting of methyl, 1-methyl-tetrazol-5-ylthiomethyl and 5-methyl-1,3,4-thiadiazol-2-ylthiomethyl. Especially preferred are the compositions when the active compound is selected from the group consisting of the syn isomer of 3-methyl-7-[2-(2-amino-4-thiazolyl)-2-(carboxymethoxyimino)-acetamido]-ceph-3-eme-4-carboxylic acid, the syn isomer of 3-[(1-methyl-tetrazol-5-yl)-thiomethyl]-7-[2-(2-amino-4-thiazolyl)-2-(carboxymethoxyimino)-acetamido]-ceph-3-eme-4-carboxylic acid and the syn isomer of 3-[(5-methyl-1,3,4-thiadiazol-2-yl)-thiomethyl]-7-[2-(2-amino-4-thiazolyl)-2-(carboxymethoxyimino)-acetamido]-ceph-3-eme-4-carboxylic acids and their alkali metal, alkaline earth metal, magnesium, $—NH_4$ and organic amine salts and easily cleavable esters.

The novel method of the invention for combatting bacterial infections in warm-blooded animals, including humans, comprises administering to warm-blooded animals an antibacterially effective amount of at least one compound of formula I and their non-toxic, pharmaceutically acceptable acid addition salts. The compounds may be administered orally, rectally, parenterally or locally by topical application to the skin or mucous. The usual daily dose is 5 to 80 mg/kg depending on the specific compound and the method of administration. The compositions are also useful for sterilizing medical instruments.

The novel intermediate compounds of the invention are those of formula IV.

The starting compounds of formula II may be prepared by reacting (a) a syn isomer of a compound of the formula

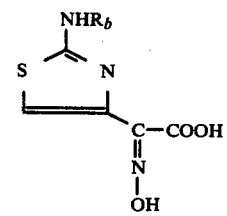

B with 2-methoxypropene to obtain a syn isomer of a compound of the formula

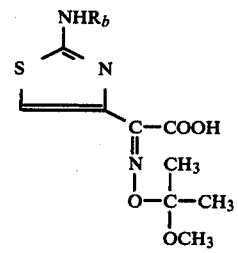

E (b) condensing the latter with a compound of formula V under the same conditions for the condensation of compounds of formulae V and VI to obtain a compound of the formula

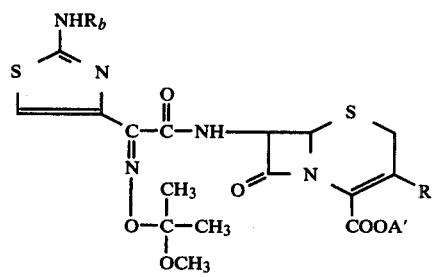

F and (c) treating the latter with an acid to obtain a compound of formula II.

The compounds of formula B are described in Belgium Patent No. 825,298 and the products of formula V are prepared by subjecting 7-amino-cephalosporanic acid to a known exchange reaction. The products of the formula VI are prepared by reacting a compound of formula III with a compound of formula B under the same conditions as the reaction of the compounds of formulae III and II.

In the following examples there are described several preferred embodiments to illustrate the invention. However, it is to be understood that the invention is not intended to be limited to the specific embodiments.

EXAMPLE 1

Trifluoroacetate of the syn isomer of 3-methyl-7-[2-(2-amino-4-thiazolyl)-2-(carboxymethyloxyimino)-acetamido]-ceph-3-eme-4-carboxylic acid STEP A: syn isomer of diethylamine 3-methyl-7-[2-(2-tritylamino-4-thiazolyl)-2-(1-methyl-1-methoxy-ethoxyimino)-acetamido]-ceph-3-eme-4-carboxylate A mixture of 33.24 g of the syn isomer of 2-(2-tritylamino-4-thiazolyl)-2-(hydroxyimino)-acetic acid, 330 ml of methylene chloride and 33 ml of 2-methoxy-propene was stirred under argon at room temperature for 15 minutes and was then evaporated to dryness under reduced pressure to obtain the syn isomer of 2-(2-tritylamino-4-thiazolyl)-2-(1-methyl-1-methoxy-ethoxyimino)-acetic acid. The residue was dissolved in 170 ml of dry methylene chloride and 8.75 g of dicyclohexylcarbodiimide were added thereto under argon. After total dissolution, dicyclohexylurea crystallized and the mixture was stirred for 100 minutes and was vacuum filtered. The filter was rinsed and the filtrate was iced and a solution A was added thereto with stirring over 3 minutes.

Solution A was prepared by stirring a mixture of 13.27 g of 7-amino-desacetoxycephalosporanic acid, 130 ml of nitromethane and 17.4 ml of dry triethylamine under argon for 5 minutes and the mixture was vacuum filtered. The product was rinsed with a minimum of nitromethane and was empasted with ether and dried to obtain 5 g of product which did not dissolve. The filtrate which was solution A contained 8.27 g of 7-amino-desacetoxy-cephalorsporanic acid.

The mixture of solution A and the filtrate stood for 3½ hours during which spontaneous heating occured and the mixture was evaporated to dryness under reduced pressure. The residue was added to 500 ml of ethyl acetate and 250 ml of N hydrochloric acid (pH=1) and the mixture was stirred for 20 minutes and was then vacuum filtered. The product was rinsed with ethyl acetate and water and dried to obtain 10.7 g of the starting material. The decanted organic filtrate was washed with aqueous sodium chloride and the wash water was extracted with 100 ml of ethyl acetate. The combined organic phases were dried and vacuum filtered and the filtrate was evaporated under reduced pressure to obtain a paste which was added to 50 ml of ethyl acetate. Complete dissolution occured and 8.5 ml of pure diethylamine were added thereto. The mixture was diluted with 300 ml of ether to effect precipitation and after cooling in ice water for 30 minutes, the mixture was vacuum filtered. The product was rinsed and dried to obtain 24.75 g of the syn isomer of diethylamine 3-methyl-7-[2-(2-tritylamino-4-thiazolyl)-2-(1-methyl-1-methoxy-ethoxyimino)-acetamido]-ceph-3-eme-4-carboxylate with an RF=0.7 (acetone containing 10% of water).

STEP B: syn isomer of 3-methyl-7-[2-(2-tritylamino-4-thiazolyl)-2-hydroxyimino-acetamido]-ceph-3-eme-4-carboxylic acid A mixture of 21 g of the product of Step A, 80 ml of acetone and 27 ml of 2 N hydrochloric acid was stirred at room temperature for 90 minutes and 55 ml of water were added thereto with stirring. The acetone was evaporated under reduced pressure and 140 ml of ethyl acetate were added with stirring. The decanted aqueous phase was extracted with ethyl acetate and the combined organic phases were washed with half saturated aqueous sodium chloride solution, was dried and vacuum filtered to obtain the syn isomer of 3-methyl-7-[2-(2-tritylamino-4-thiazolyl)-2-hydroxyiminoacetamido]-ceph-3-eme-4-carboxylic acid.

STEP C: syn isomer of diethylamine 3-methyl-7[2-(2-tritylamino-4-thiazolyl)-2-(tert.-butoxycarbonylmethoxyimino)-acetamido]-ceph-3-eme-4-carboxylate 4.7 g of the product of Step B were added to 70 ml of methylene chloride and then 70 ml of distilled water were added thereto. 21 ml of trithylamine were added thereto with stirring and under reduced pressure and after 5 minutes of stirring, 15.3 ml of tert.-butyl bromoacetate were added thereto all at once. The mixture was vigorously stirred at 25°–30° C. for 30 minutes and was then acidified at 15°–20° C. by addition of 8 ml of hydrochloric acid. The decanted aqueous phase was extracted twice with 20 ml of methylene chloride and the combined organic phases were washed 3 times with 50 ml of distilled water, was dried over magnesium sulfate and was vacuum filtered. The filtrate was rinsed and the filtrate was evaporated to dryness under reduced pressure. The 9.8 g of gum were dissolved in 30 ml of ethyl acetate and the mixture was stirred at 20° C. until dissolution occured. 0.75 ml of diethylamine were added thereto followed by the addition of 60 ml of isopropyl ether and the mixture was stirred at 20°–25° C. for 15 minutes and was then vacuum filtered. The recovered product was washed twice with 5 ml of a 1-2 ethyl acetate-isopropyl ether mixture and 3 times with 10 ml of isopropyl ether and was dried to obtain 4.31 g of the syn isomer of diethylamine 3-methyl-7-[2-(2-tritylamino-4-thiazolyl)-2-(tert.-butoxycarbonylmethoxyimino)-acetamido]-ceph-3-eme-4-carboxylate melting at 140° C. (decomposition).

RMN Spectrum (deuterochloroform): peaks at 7.3 ppm (trityl protons); at 6.81 ppm (5-proton of thiazole); at 4.73 ppm (O—C$\underline{H}_2$—COO-tert.-butyl).

STEP D: Trifluoroacetate of syn isomer of 3-methyl-7-[2-(2-amino-4-thiazolyl)-2-(carboxymethyloxyimino)-acetamido]-ceph-3-eme-4-carboxylic acid A mixture of 4.26 g of the product of Step C and 42 ml of trifluoroacetic acid was stirred at 20°–25° C. for 15 minutes and was then evaporated under reduced pressure at less than 30° C. to a volume of 10 to 15 ml. 100 ml of ether were added thereto all at once with stirring and the mixture was stirred at 20° C. for 15 minutes and was then vacuum filtered. The product was rinsed 5 times with 10 ml of isopropyl ether and was dried under reduced pressure at room temperature to obtain 2.47 g of raw product. The latter was taken up in 10 ml of acetone containing 1% of water and the mixture was stirred at 20°–25° C. for 5 minutes to obtain a homogeneous suspension which was diluted with 100 ml of ether at 20°–25° C. The mixture was vacuum filtered at 20° C. and was rinsed 3 times with 5 ml of ether and dried under reduced pressure to obtain 2.01 g of the trifluoroacetate of syn isomer of 3-methyl-7-[2-(2-amino-4-thiazolyl)-2-(carboxymethyloxyimino)-acetamido]-ceph-3-eme-4-carboxylic acid with an Rf=0.3 (acetone containing 10% of water).

EXAMPLE 2 syn isomer of disodium 3-methyl-7-[2-(2-amino-4-thiazolyl)-2-carboxymethyloxyimino)-acetamido]-ceph-3-eme-4-carboxylate A mixture of 2.01 g of the product of Example 1, 14.5 ml of a molar sodium acetate in methanol solution and 40 ml of methanol was stirred and filtered and the filter was rinsed 3 times with 1 ml of methanol. The filtrate was evaporated under reduced pressure at less than 30° C. to a volume of 2 ml and was then diluted with 100 ml of pure ethanol added all at once with stirring. The mixture was vacuum filtered and the recovered product was rinsed 3 times with 5 ml of ethanol and 3 times with 10 ml of ether and was dried under reduced pressure to obtain 1.53 g of the syn isomer of disodium 3-methyl-7-[2-(2-amino-4-thiazolyl)-2-carboxymethyloxyimino)-acetamido]-ceph-3-eme-4-carboxylate with a specific rotation of $[\alpha]_D^{20} = +75° \pm 1.5°$ (c=1% in water).

RMN Spectrum (DMSO): peaks at 4.26 ppm (=NOCH$_2$—); at 6.81 ppm (5-proton of thiazole)

EXAMPLE 3

Trifluoroacetate of syn isomer of 3-[(1-methyl-tetrazol-5-yl)-thiomethyl]-7-[2-(2-amino-4-thiazolyl)-2-(carboxymethyloxyimino)-acetamido]-ceph-3-eme-4-carboxylic acid STEP A: syn isomer of 3-[(1-methyl-tetrazol-5-yl)-thiomethyl]-7-[2-(2-tritylamino-4-thiazolyl)-2-(1-methyl-1-methoxyethoxyimino)-acetamido]-ceph-3-eme-4-carboxylic acid A mixture of 4.3 g of the syn isomer of 2-(2-tritylamino-4-thiazolyl)-2-hydroxyimino-acetic acid, 25 ml of methylene chloride and 4 ml of 2-methoxypropene was stirred at room temperature for 20 minutes and was evaporated to dryness. The residue was added to 25 ml of methylene chloride and 1.1 g of dicyclohexylcarbodiimide were added thereto. The mixture was stirred at room temperature for 50 minutes and was vacuum filtered to remove 0.8 g of dicyclohexylurea. The filtrate was cooled to −30° C. and a solution of 1.64 g of 3-(1-methyl-tetrazol-5-yl)-thiomethyl-7-amino-cephalosporanic acid in 8 ml of methylene chloride and 1.2 ml of triethylamine was added thereto at −30° C. The temperature returned to room temperature over 90 minutes and 20 ml of ethyl acetate were added thereto. The mixture was stirred with 20 ml of N hydrochloric acid for 10 minutes during which excess starting acid precipitated. The mixture was vacuum filtered and the filtrate was dried and evaporated to dryness to obtain the syn isomer of 3-[(1-methyl-tetrazol-5-yl)-thiomethyl]-7-[2-(2-tritylamino-4-thiazolyl)-2-(1-methyl-1-methoxy-ethoxyimino)-acetamido]-ceph-3-eme-4-carboxylic acid STEP B: syn isomer of 3-[(1-methyl-tetrazol-5-yl)-thiomethyl]-7-[2-(2-tritylamino-4-thiazolyl)-2-hydroxyimino-acetamido]-ceph-3-eme-4-carboxylic acid The product of Step A was taken up in 10 ml of ethyl acetate and 0.5 ml of diethylamine were added thereto. 100 ml of ether were added to the mixture which was vacuum filtered to obtain 2.748 g of the syn isomer of diethylamine 3-[(1-methyl-tetrazol-5-yl)-thiomethyl]-7-[2-(2-tritylamino-4-thiazolyl)-2-(1-methyl-1-methoxy-ethoxyimino)-acetamido]-ceph-3-eme-4-carboxylate which was added to 10 ml of acetone and 3.5 ml of N hydrochloric acid. The mixture was stirred for 40 minutes and the acetone was evaporated. The mixture was extracted with ethyl acetate and the organic phase was dried and evaporated to a small volume. 50 ml of ether were added thereto and the mixture was vacuum filtered to obtain 1.83 g of the syn isomer of 3-[(1-methyl-tetrazol-5-yl)-thiomethyl]-7-[2-(2-tritylamino-4-thiazolyl)-2-hydroxyimino-acetamido]-ceph-3-eme-4-carboxylic acid.

STEP C: syn isomer of diethylamine 3-[(1-methyl-tetrazol-5-yl)-thiomethyl]-7-[2-(2-tritylamino-4-thiazolyl)-2-(tert.-butoxycarbonylmethyloxyimino)-acetamido]-ceph-3-eme-4-carboxylate 55 ml of distilled water were added to a solution of 3.7 g of the product of Step B in 55 ml of methylene chloride and 7 ml of triethylamine followed by 4 ml of tert.-butyl bromoacetate were added thereto with vigorous stirring. The mixture was vigorously stirred for 2 hours at 20°–25° C. and was then acidified at 20°–25° C. with 15 ml of 2 N hydrochloric acid. The decanted aqueous phase was extracted twice with 20 ml of methylene chloride and the combined organic phases were washed 3 times with 50 ml of distilled water to obtain neutral wash waters, was dried and vacuum filtered. The filter was rinsed and the filtrate was evaporated to dryness under reduced pressure to obtain 4.35 g of raw product. The latter was added to 45 ml of ethyl acetate and the mixture was stirred at room temperature to obtain a slightly turbid solution. 0.5 ml of diethylamine were added thereto at 20°–25° C. and the brown gum was decanted and rinsed twice with 5 ml of ethyl acetate to obtain 0.7 g of product. 110 ml of isopropyl ether were added to the solution and the mixture was stirred at 20°–25° C. for 30 minutes and was vacuum filtered. The product was rinsed twice with 5 ml of a 2-1 isopropyl ether-ethyl acetate mixture and three times with 10 ml of isopropyl ether and was dried at room temperature under reduced pressure to obtain 2.52 g of the syn isomer of diethylamine 3-[(1-methyl-tetrazol-5-yl)-thiomethyl]-7-[2-(2-tritylamino-4-thiazolyl)-2-(tert.-butoxycarbonylmethyloxyimino)-acetamido]-ceph-3-eme-4-carboxylate melting at 150° C. (decomposition).

RMN Spectrum (deuterochloroform): peaks at 7.28 ppm (trityl); at 6.81 ppm (5-proton of thiazole); at 4.75 ppm (=NO—CH$_2$—).

STEP D: trifluoroacetate of syn isomer of 3-[(1-methyltetrazol-5-yl)-thiomethyl]-7-[2-(2-amino-4-thiazolyl)-2-(carboxymethyloxyimino)-acetamido-]-ceph-3-eme-4-carboxylic acid A mixture of 2.7 g of the product of Step C and 27 ml of trifluoroacetic acid was stirred in a flask at 20°–22° C. for 15 minutes during which total dissolution rapidly occured and the mixture was evaporated under reduced pressure at less than 30° C. to a volume of 10 ml. 100 ml of isopropyl ether were added thereto all at once and the mixture was stirred at room temperature for 15 minutes and was then vacuum filtered. The product was rinsed 5 times with 10 ml of isopropyl ether to obtain 1.9 g of raw product which was empasted with 10 ml of acetone containing 1% water at room temperature for 5 minutes. Then, 100 ml of ether were added thereto and the mixture was vacuum filtered. The recovered product was rinsed 3 times with 5 ml of ether and was dried under reduced pressure to obtain 1.44 g of the trifluoroacetate of syn isomer of 3-[(1-methyl-tetrazol-5-yl)-thiomethyl]-7-[2-(2-amino-4-thiazolyl)-2-(carboxymethyloxyimino)-acetamido]-ceph-3-eme-4-carboxylic acid with an Rf=0.4 (acetone containing 10% water).

EXAMPLE 4 syn isomer of
3-[(1-methyl-tetrazol-5-yl)-thiomethyl]-7-[2-(2-amino-4-thiazolyl)-2-(carboxymethyloxyimino)-acetamido]-ceph-3-eme-4-carboxylic acid A mixture of 1.44 g of the product of Exampel 3, 8 ml of a 1-1 methanol-methylene chloride mixture and 2.2 ml of a molar solution of pyridine in ethanol was empasted in a flask for 15 minutes at room temperature to obtain incomplete dissolution and 40 ml of ether containing 2% of ethanol were added thereto at room temperature over 2 minutes. The mixture was stirred at 20°–25° C. for 30 minutes and was vacuum filtered. The recovered product was washed 3 times with 10 ml of ether and was dried at room temperature to obtain 1.35 g of the syn isomer of 3-[(1-methyl-tetrazol-5-yl)-thiomethyl]-7-[2-(2-amino-4-thiazolyl)-2-(carboxymethyloxyimino)-acetamido]-ceph-3-eme-4-carboxylic acid with an Rf=about 0.4 (acetone with 10% water).

EXAMPLE 5 syn isomer of disodium
3-[(1-methyl-tetrazol-5-yl)-thiomethyl]-7-[2-(2-amino-4-thiazolyl)-2-(carboxymethoxyimino)-acetamido]-ceph-3-eme-4-carboxylate 0.15 g of animal black were added at room temperature to a solution of 1.35 g of the product of Example 4, 9.7 ml of a molar solution of sodium acetate in methanol and 28 ml of methanol containing 10% water and the mixture was stirred and vacuum filtered. The product was rinsed 3 times with 1 ml of methanol containing 10% water and 3 times with 5 ml of methanol. The filtrate was concentrated under reduced pressure at less than 30° C. to a volume of 10 ml and 50 ml of ethanol were slowly added thereto at 20°–25° C. The suspension was stirred for 15 minutes at room temperature and was vacuum filtered. The product was rinsed 3 times with 5 ml of ethanol and 3 times with 10 ml of ether and was dried under reduced pressure to obtain 1.05 g of the syn isomer of disodium 3-[(1-methyl-tetrazol-5-yl)-thiomethyl]-7-[2-(2-amino-4-thiazolyl)-2-(carboxymethyloxyimino)-acetamido]-ceph-3-eme-4-carboxylate with a specific rotation of $[\alpha]_D^{20} = -16.5° \pm 1°$ (c=1% in water).

RMN Spectrum (DMSO): peaks at 6.83 ppm (5-proton of thiazol).

EXAMPLE 6

Trifluoroacetate of syn isomer of
3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylic acid STEP A: syn isomer of diethylamine
3-[(5-methyl-1,3,4-thiadiazol-2-yl)-thiomethyl]-7-[2-(2-tritylamino-4-thiazolyl)-2-(hydroxyimino)-acetamido]-ceph-3-eme-4-carboxylate 0.23 g of dicyclohexylcarbodiimide were added under argon at 20° C. to a mixture of 1.002 g of the syn isomer of 2-(2-tritylamino-4-thiazolyl)-2-(1-methyl-1-methoxy-ethoxyimino)-acetic acid and 3 ml of methylene chloride and the mixture was stirred at 20°–25° C. for one hour to obtain a suspension of dicyclohexylurea. In a second flask, 0.28 ml of triethylamine were added at 20° to 25° C. to a suspension of 0.344 g of 3-[(5-methyl-1,3,4-thiadiazol-2-yl)-thiomethyl]-7-amino-ceph-3-eme-4-carboxylic acid in 2 ml of nitromethane to form a brown solution which was added over 5 minutes with stirring at 20°–25° C. to the first suspension. The mixture was rinsed with methylene chloride and was then stirred for 2 hours and was vacuum filtered to remove dicyclohexylurea (0.2 g). The filter was rinsed with methylene chloride and the filtrate and 8 ml of N hydrochloric acid were stirred. The mixture was vacuum filtered and the brown product was rinsed with water and methylene chloride to obtain 0.4 g of mainly the starting product. The filtrate was washed with distilled water until the wash water was neutral, dried and distilled to dryness under reduced pressure. The residue was added to 5 ml of ethyl acetate and the mixture was vacuum filtered at room temperature. The product was rinsed with ethyl acetate to obtain 0.32 g of the syn isomer of 2-(2-tritylamino-4-thiazolyl)-2-hydroxyimino-acetic acid.

The filtrate was concentrated to a volume of 4 ml and 0.1 ml of diethylamine was added thereto. 9 ml of isopropyl ether were added thereto at 20° C. and the mixture was stirred at 20°–25° C. for one hour and was vacuum filtered. The product was rinsed with ethyl acetate and isopropyl ether and dried under reduced pressure to obtain 0.72 g of the syn isomer of diethylamine 3-[(5-methyl-1,3,4-thiadiazol-2-yl)-thiomethyl]-7-[2-(2-tritylamino-4-thiazolyl)-2-(hydroxyimino)-acetamido]-ceph-3-eme-4-carboxylate.

RMN Spectrum (deuterochloroform): peaks at 6.76 ppm (5-proton of thiazolyl); at 7.28 ppm (trityl protons).

STEP B: syn isomer of
3-[(5-methyl-1,3,4-thiadiazol-2-yl)-thiomethyl]-7-[2-(2-tritylamino-4-thiazolyl)-2-(hydroxyimino)-acetamido]-ceph-3-eme-4-carboxylic acid 8.6 ml of 2 N hydrochloric acid were added at 20°–25° C. to a solution of 6.93 g of the product of Step B in 28 ml of acetone and the mixture was stirred at 20°–23° C. for 2½ hours. Then, 4.3 ml of 2 N hydrochloric acid and then 28 ml of distilled water were added thereto and the acetone was evaporated at less than 35° C. The mixture was vacuum filtered at room temperature and the product was washed until the wash water was neutral and wash evaporated under reduced pressure to obtain 5.79 g of raw product. 2.79 g of the product were dissolved in 8.4 ml of methylene chloride and 28 ml of ethyl acetate were added thereto at 20°–25° C. over 5 minutes. The mixture was stirred for 30 minutes and was vacuum filtered. The product was rinsed with ethyl acetate and dried under reduced pressure to obtain 2.2 g of the syn isomer of 3-[(5-methyl-1,3,4-thiadiazol-2-yl)-thiomethyl]-7-[2-(2-tritylamino-4-thiazolyl)-2-(hydroxyimino)-acetamido]-ceph-3-eme-4-carboxylic acid. Concentration of the filtrate under reduced pressure to about 5 ml and vacuum filtration yielded another 0.27 g of the product.

RMN Spectrum (deuterochloroform): 60 MHz peaks at 7.01 ppm (5-proton of thiazole); at 7.31 ppm (trityl protons).

STEP C: syn isomer of diethylamine 3-[(5-methyl-1,3,4-thiadiazol-2-yl)-thiomethyl]-7-[2-(2-tritylamino-4-thiazolyl)-2-(tert.-butoxycarbonyl-methyloxyimino)-acetamido]-ceph-3-eme-4-carboxylate 42 ml of distilled water were added at room temperature to a stirred mixture of 2.78 g of the product of Step B in 42 ml of methylene chloride in a flask and 5.1 ml of triethylamine were added thereto with vigorous stirring. The mixture was stirred 3 minutes to obtain an emulsion to which 3.2 ml. of tert.-butyl bromoacetate were added at 18°-20° C. The mixture was vigorously stirred at 22° C. for 100 minutes and was acidified to about a pH of 1 at 20° C. by addition of 10 ml of 2 N hydrochloric acid. The decanted aqueous phase was extracted twice with 20 ml of methylene chloride and the combined organic phases were washed with water until the wash water was neutral and the wash waters were extracted with methylene chloride. The organic phase was dried and evaporated to dryness to obtain 4.3 g of product which was taken up in 4 ml of methylene chloride. 40 ml of ethyl acetate were added at 20° C. to the solution and 0.37 ml of diethylamine were added all at once to the solution. The mixture was vacuum filtered and the product was rinsed twice with 5 ml of ethyl acetate and was dried under reduced pressure to obtain the diethylamine salt of the starting material. 100 ml of isopropyl ether were added to the filtrate at 20° C. and the mixture was stirred at 20°-25° C. for one hour and was vacuum filtered. The recovered product was washed twice with 5 ml of a 1-2 ethyl acetate-isopropyl ether mixture and 3 times with 10 ml of isopropyl ether and dried at 40° C. under reduced pressure to obtain 2.36 g of the syn isomer of diethylamine 3-[(5-methyl-1,3,4-thiadiazol-2-yl)-thiomethyl]-7-[2-(2-tritylamino-4-thiazolyl)-2-(tert.-butyoxycarbonyl-methyloxyimino)-acetamido]-ceph-3-eme-4-carboxylate melting at 160° C.

RMN Spectrum (deuterochloroform): peaks at 7.26 ppm (trityl); at 4.71 ppm (=N—O—C$\underline{H}_2$).

STEP D: Trifluoroacetate of syn isomer of 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylic acid A mixture of 2.3 g of the product of Step C and 23 ml of trifluoroacetic acid was stirred at 20°-23° C. for 15 minutes and was then evaporated under reduced pressure at less than 30° C. to a volume of 8 ml. 100 ml of isopropyl ether were added all at once with stirring to the mixture which was stirred at 20° C. for 15 minutes and was vacuum filtered at 20° C. The product was rinsed 5 times with 10 ml of isopropyl ether and dried under reduced pressure at room temperature to obtain 1.63 g of raw product. Then 1.53 g of the latter was empasted with 7 ml of acetone containing 1% water at room temperature for 5 minutes and 70 ml of ether were added thereto with stirring at 20°-25° C. The mixture was vacuum filtered and the product was rinsed 3 times with 10 ml of ether and was dried under reduced pressure at room temperature to obtain 1.26 g of the trifluoroacetate of syn isomer of 3-[(5-methyl-1,3,4-thiadiazol-2-yl)-thiomethyl]-7-[2-(2-amino-4-thiazolyl)-2-carboxymethyloxyimino-acetamido]-ceph-3-eme-4-carboxylic acid.

EXAMPLE 7 syn isomer of 3-[(5-methyl-1,3,4-thiadiazol-2-yl)-thiomethyl]-7-[(2-amino-4-thiazolyl)-2-(carboxymethyloxyimino)-acetamido]-ceph-3-eme-4-carboxylic acid 2 ml of a molar solution of pyridine in ethanol were slowly added at 20°-25° C. to a mixture of 1.26 g of the product of Example 6 and 6 ml of a 1-1 methylene chloride-methanol mixture and the mixture was stirred for 5 minutes at room temperature. 50 ml of ether containing 2% of ethanol were added thereto with stirring at 20°-25° C. and the mixture was stirred at 20°-25° C. for one hour and was then vacuum filtered. The recovered product was rinsed 3 times with 2 ml of ether containing 2% of ethanol and 3 times with 10 ml of ether and was dried at room temperature under reduced pressure to obtain 1.1 g of the syn isomer of 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylic acid.

EXAMPLE 8 syn isomer of disodium 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylate 0.1 g of animal black was added at room temperature to a stirred solution of 1.1 g of the product of Example 7, 25 ml of methanol and 7.7 ml of a solution of sodium acetate in methanol and the mixture was vacuum filtered. The filter was rinsed with methanol and the filtrate was evaporated under reduced pressure at less than 30° C. to a volume of about 5 ml. 50 ml of pure ethanol were added thereto at room temperature and the mixture was stirred at 20°-25° C. for 15 minutes and was vacuum filtered. The product was rinsed 3 times with 5 ml of pure ethanol and 3 times with 10 ml of ether and was dried under reduced pressure to obtain 0.965 g of the syn isomer of disodium 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylate with a specific rotation of $[\alpha]_D^{20} = -55.5° \pm 1.5°$ (c=1% in water).

RMN Spectrum (DMSO): peaks at 4.25 ppm (=N—OC$\underline{H}_2$—COO$^-$); at 6.82 ppm (5-proton of thiazole).

EXAMPLE 9

Injectable solutions were prepared from 500 mg of either the syn isomer of disodium 3-[(1-methyl-tetrazol-5-yl)-thiomethyl]-7-[2-(2-amino-4-thiazolyl)-2-(carboxymethyloxyimino)-acetamido]-ceph-3-eme-4-carboxylate or the syn isomer of disodium 3-[(5-methyl-1,3,4-thiadiazol-2-yl)-thiomethyl]-7-[2-(2-amino-4-thiazolyl)-2-(carboxymethyloxyimino)-acetamido]-ceph-3-eme-4-carboxylate and sufficient sterile water for a final volume of 5 ml.

Gelules were prepared with 250 mg of the syn isomer of disodium 3-[(1-methyl-tetrazol-5-yl)-thiomethyl]-7-[2-(2-amino-4-thiazolyl)-2-(carboxymethyloxyimino)-acetamido]-ceph-3-eme-4-carboxylate and sufficient excipient for a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 or 48 hours at 37° C. in an oven. The increasing inhibition was determined by transillumination to determine the minimum inhibiting concentration (MIC in µg/ml) and the results are reported in the following Tables.

|  | M.I.C. in µg/ml | | | | | |
|---|---|---|---|---|---|---|
|  | PRODUCT OF EXAMPLE 2 | | PRODUCT OF EXAMPLE 5 | | PRODUCT OF EXAMPLE 8 | |
| STRAINS | 24h | 48h | 24h | 48h | 24h | 48h |
| Staphylococcus aureus ATCC 6 538 Pen-Sensible | >40 | >40 | 2 | 2 | 3 | 5 |
| Staphylococcus aureus UC 1 128 Pen-Résistant | >40 | >40 | 3 | 3 | 5 | 10 |
| Staphylococcus aureus exp. n°54 146 | >40 | >40 | 2 | 2 | 5 | 5 |
| Streptococcus pyogènes A 561 | 1 | 1 | 0,1 | 0,1 | 0,2 | 0,5 |
| Streptococcus faecalis 5 432 | >40 | >40 | 20 | 40 | 20 | >40 |
| Streptococcus faecalis 99 F 74 | >40 | >40 | 20 | >40 | >40 | >40 |
| Bacillus subtilis ATCC 6 633 | >40 | >40 | 1 | 5 | 5 | 5 |
| Escherichia Coli Sensible Tétracycline ATCC 9 637 | 0,5 | 0,5 | 0,2 | 0,2 | 0,2 | 0,2 |
| Escherichia Coli Résistant Tétracycline ATCC 11 303 | 0,2 | 2 | 0,05 | 0,2 | 0,05 | 0,1 |
| Escherichia Coli Exp. TO26B6 | 0,2 | 0,5 | 0,2 | 0,2 | 0,2 | 0,2 |
| Escherichia Coli Résistant Gentamycine, Tobramycine R 55 123 D | 2 | 2 | 0,2 | 0,5 | 0,2 | 0,2 |
| Klebsiella pneumoniae Exp. 52 145 | 0,2 | 0,2 | 0,05 | 0,1 | 0,5 | 0,5 |
| Klebsiella pneumoniae 2 536 Résistant Gentamycine | 0,2 | 0,5 | 0,2 | 0,2 | 0,2 | 0,5 |
| Proteus mirabilis (indol −) A 235 | 0,2 | 0,2 | 0,02 | 0,05 | 0,05 | 0,05 |
| Proteus vulgaris (indol +) A 232 | 1 | 1 | 0,1 | 0,1 | 0,1 | 0,2 |
| Salmonella typhimurium 420 | 1 | 1 | 0,1 | 0,1 | 0,2 | 0,2 |
| Enterobacter cloacae 681 | >40 | >40 | 2 | 5 | 1 | 1 |
| Providencia Du 48 | 0,5 | 0,5 | 2 | 2 | 0,5 | 1 |
| Serratia Résistant Gentamycine 2 532 | 1 | 2 | 0,2 | 0,2 | 1 | 1 |

Various modifications of the products and processes of the invention may be made without departing from the spirit or scope thereof and it is to be understood that the invention is intended to be limited only as defined in the appended claims.

We claim:

1. A compound selected from the group consisting of syn isomers of 7-[2-(2-amino-4-thiazolyl)-2-(carboxymethyloxyimino)-acetamido]-ceph-3-eme-4-carboxylic acid compounds of the formula

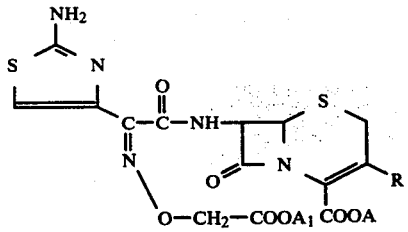

wherein R is alkyl of 1 to 3 carbon atoms, A is selected from the group consisting of hydrogen, alkali metal, alkaline earth metal, —NH4, an easily cleavable ester and a non-toxic, pharmaceutically acceptable organic amine, A1 is selected from the group consisting of alkyl of 1 to 3 carbon atoms, hydrogen, alkali metal, alkaline earth metal, —NH4, an easily cleavable ester and a non-toxic, pharmaceutically acceptable organic amine and non-toxic, pharmaceutically acceptable acid addition salts thereof.

2. A compound of claim 1 wherein R is methyl.

3. A compound of claim 1 selected from the group consisting of the syn isomer of 3-methyl-7-[2-(2-amino-4-thiazolyl)-2-(carboxymethyloxyimino)-acetamido]-ceph-3-eme-4-carboxylic acid and its alkali metal, alkaline earth metal, —NH4 and organic amine salt and easily cleavable esters.

4. An antibiotic composition comprising an antibiotically effective amount of at least one compound of claim 1 and an inert pharmaceutical carrier.

5. A composition of claim 4 wherein R is methyl.

6. A composition of claim 4 wherein the active compound is selected from the group consisting of the syn isomer of 3-methyl-7-[2-(2-amino-4-thiazolyl)-2-(carboxymethyloxyimino)-acetamido]-ceph-3-eme-4-carboxylic acid and its alkali metal, alkaline earth metal, —NH4 and organic amine salts and easily cleavable esters.

7. A method of treating bacterial infections in warm-blooded animals comprising administering an antibiotically effective amount of at least one compound of claim 1.

8. The method of claim 7 wherein R is methyl.

9. The method of claim 7 wherein the compound is selected from the group consisting of the syn isomer of 3-methyl-7-[2-(2-amino-4-thiazolyl)-2-(carboxymethyloxyimino)-acetamido]-ceph-B 3-eme-4-carboxylic acid and its alkali metal, alkaline earth metal, —NH4 and organic amine salts and easily cleavable esters.

* * * * *

UNITED STATES PATENT AND TRADEMARK OFFICE
CERTIFICATE OF CORRECTION

PATENT NO. : 4,374,834
DATED : February 22, 1983   Page 1 of 2
INVENTOR(S) : RENE HEYMES ET AL.

It is certified that error appears in the above-identified patent and that said Letters Patent is hereby corrected as shown below:

Title page [30], Foreign Application Priority Data "78 10287"
                     should read -- 78 10387 --.

Column 2, lines 32 and 33: "methox-" should read -- methoxy- --.

Column 2, lines 33, 38; Column 4, line 37:
                 "ymethyl" should read -- methyl --.

Column 2, line 34: "yethyl" should read -- ethyl --.

Column 2, line 37, "isobutyrylox" should read -- isobutyroxy- --

Column 2, line 57; Column 12, line 53; Column 13, lines 12, 35"
                 "thi-" should read -- thio- --.

Column 2, line 58; Column 12, line 54; Column 13, lines 13, 36:
                 "omethyl" should read -- methyl --.

Column 2, line 61; Column 8, lines 1, 4; Column 16, lines 7, 62:
                 "carbox-" should read -- carboxy- --.

Column 2, line 62; Column 16, lines 8 and 63: "ymethyloxyimino"
                 should read -- methyloxyimino --.

Column 4, line 19: "phenyla-" should be -- phenyl- --.
Column 4, line 20: "cetyl" should read -- acetyl --.
Column 4, line 36: "pivaloylox-" should be -- pivaloyloxy- --.
Column 5, line 7: "benzylox-" should read -- benzyloxy- --.
Column 5, line 88: "ycarbonyl" should read -- carbonyl --.
Column 5, line 62: "phenox-" should read -- phenoxy- --.
Column 5, line 63: "ybutyric" should read -- butyric --.

UNITED STATES PATENT AND TRADEMARK OFFICE
CERTIFICATE OF CORRECTION

PATENT NO. : 4,374,834
DATED : February 22, 1983
INVENTOR(S) : RENE HEYMES ET AL.

Page 2 of 2

It is certified that error appears in the above-identified patent and that said Letters Patent is hereby corrected as shown below:

Column 8, lines 2 and 5: "ymethoxyimino" should read
-- methoxyimino --.
Column 10, line 4: "hydrox-" should read -- hydroxy- --.
Column 10, line 5; Column 11, line 44: "yimino" should read
-- imino --.
Column 10, line 28: "brom-" should read -- bromo- --.
Column 10, line 29; Column 16, line 6: "oacetate" should read
-- acetate --.
Column 11, line 43: "methoxyethox-" should read
-- methoxyethoxy- --.
Column 16, line 5: "trifluor-" should read -- trifluoro- --.
Column 18, line 5 of Claim 3: "salt" should read -- salts --.

Signed and Sealed this

Thirty-first Day of January 1984

[SEAL]

Attest:

GERALD J. MOSSINGHOFF

Attesting Officer       Commissioner of Patents and Trademarks